(12) United States Patent
Jagadish et al.

(10) Patent No.: US 10,289,868 B2
(45) Date of Patent: May 14, 2019

(54) TRANSMITTING MEDICAL DATASETS

(71) Applicants: Vilasa Palleda Jagadish, Erlangen (DE); Naveen Ramamurthy, Erlangen (DE); Chandrashekara Rangapura Shettappa, Erlangen (DE)

(72) Inventors: Vilasa Palleda Jagadish, Erlangen (DE); Naveen Ramamurthy, Erlangen (DE); Chandrashekara Rangapura Shettappa, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 371 days.

(21) Appl. No.: 14/944,314

(22) Filed: Nov. 18, 2015

(65) Prior Publication Data

US 2016/0154977 A1    Jun. 2, 2016

(30) Foreign Application Priority Data

Nov. 27, 2014    (IN) .......................... 3449/DEL/2014

(51) Int. Cl.
*G06F 21/62*    (2013.01)
*G16H 10/60*    (2018.01)

(52) U.S. Cl.
CPC ......... *G06F 21/6254* (2013.01); *G16H 10/60* (2018.01)

(58) Field of Classification Search
CPC ............................ G06F 21/6254; G06F 19/322
See application file for complete search history.

(56) References Cited

U.S. PATENT DOCUMENTS

| | | | |
|---|---|---|---|
| 9,223,995 B1 * | 12/2015 | Lavinio | G06F 21/606 |
| 2004/0078238 A1 * | 4/2004 | Thomas | G06F 19/321 |
| | | | 705/3 |
| 2007/0192139 A1 * | 8/2007 | Cookson | G06Q 10/10 |
| | | | 705/3 |
| 2008/0021834 A1 * | 1/2008 | Holla | G06F 19/322 |
| | | | 705/51 |
| 2008/0040151 A1 * | 2/2008 | Moore | G06F 19/324 |
| | | | 705/2 |
| 2008/0077604 A1 * | 3/2008 | Bharara | G06F 19/321 |
| 2008/0147554 A1 * | 6/2008 | Stevens | G06F 21/6254 |
| | | | 705/51 |
| 2008/0301805 A1 * | 12/2008 | Bharara | G06F 19/321 |
| | | | 726/21 |

(Continued)

FOREIGN PATENT DOCUMENTS

WO    WO2013123086 A1    8/2013

*Primary Examiner* — Hee K Song
(74) *Attorney, Agent, or Firm* — Lempia Summerfield Katz LLC

(57) ABSTRACT

The present embodiments relate to a method for transmitting medical datasets. The method includes receiving a patient dataset from an internal data storage, the patient dataset including patient identification data and patient examination data. The method further includes generating an anonymized patient dataset by segregating the patient identification data from the received patient dataset. The method further includes generating an encrypted patient identification dataset on the basis of the segregated patient identification data. The method further includes transmitting the anonymized patient dataset and the encrypted patient identification dataset to an external data storage.

7 Claims, 8 Drawing Sheets

(56) References Cited

U.S. PATENT DOCUMENTS

| | | | |
|---|---|---|---|
| 2011/0119088 A1 | 5/2011 | Gunn | |
| 2012/0173317 A1* | 7/2012 | Kelley | G06Q 30/0241 705/14.4 |
| 2012/0179908 A1* | 7/2012 | Duma | G06F 19/00 713/165 |
| 2012/0191749 A1* | 7/2012 | New | G06F 17/30477 707/769 |
| 2013/0208955 A1* | 8/2013 | Zhao | G06F 19/321 382/128 |
| 2013/0212661 A1* | 8/2013 | Neafsey | G06F 21/45 726/6 |
| 2014/0188514 A1* | 7/2014 | Balignasay | G06F 19/321 705/3 |
| 2014/0195804 A1* | 7/2014 | Hursti | H04L 63/0428 713/168 |

* cited by examiner

TRANSMITTING MEDICAL DATASETS

CROSS-REFERENCE TO RELATED APPLICATIONS

This application claims the benefit of Indian Patent Application No. 3449/DEL/2014, filed on Nov. 27, 2014, which is hereby incorporated by reference in its entirety.

TECHNICAL FIELD

The present embodiments relate to a method for transmitting medical datasets.

BACKGROUND

U.S. Patent Publication No. 2011/0119088 A1 relates to a method for exchanging health information over a health exchange system. The health exchange system serves for exchanging medical information between different units that is stored in different formats. The exchange system provides a channel for the flow of information and patient datasets across different health institutions that store patient data in different formats.

SUMMARY AND DESCRIPTION

The scope of the present invention is defined solely by the appended claims and is not affected to any degree by the statements within this summary. The present embodiments may obviate one or more of the drawbacks or limitations in the related art.

It is an object of the present embodiments to anonymize personalized medical datasets in a fast manner with low deployment of technical resources.

This object is solved by a method for transmitting medical datasets, including the acts of receiving a patient dataset that includes patient identification data and patient examination data from an internal data storage; generating an anonymized patient dataset by segregating the patient identification data from the received patient dataset; generating an encrypted patient identification dataset on the basis of the patient identification data; and transmitting the anonymized patient dataset and the encrypted patient identification dataset to an external data storage. Thereby, for example, the technical advantage is achieved that datasets may be made accessible anonymously in a technically easy way. The removed patient identification data are protected by encryption and are still made available for authorized users.

In an embodiment, the anonymized patient dataset and the encrypted patient identification dataset are stored in the external data storage. Thereby, for example, the technical advantage is achieved that the anonymized patient dataset and the patient identification dataset may be stored in a central data storage, such as a cloud.

In a further embodiment of the method, the anonymized patient dataset includes a logical link to the patient identification dataset. Thereby, for example, the technical advantage is achieved that the patient identification dataset corresponding to the anonymized patient dataset may be determined.

In a further embodiment of the method, the patient identification dataset includes a logical link to the anonymized patient dataset. Thereby, for example, the technical advantage is achieved that the anonymized patient dataset corresponding to the patient identification dataset may be determined.

In a further embodiment of the method, the received and/or the anonymized patient dataset is a DICOM-file. Thereby, for example, the technical advantage is achieved that an especially suitable format for storing and for exchanging information in medical picture data management is used.

In a further embodiment of the method, the patient identification dataset is a JavaScript-Object-Notation-file. Thereby, for example, the technical advantage is achieved that a compact data format in a readily readable text form is used for the purpose of data exchange between applications.

In a further embodiment of the method, the anonymized patient dataset and the encrypted patient identification dataset are stored in the internal data storage. Thereby, for example, the technical advantage is achieved that the patient data are additionally stored locally.

In a further embodiment of the method, a user authorization is validated prior to a transmitting the anonymized patient dataset and the patient identification dataset. Thereby, for example, the technical advantage is achieved that only authorized users gain access to the patient data.

In a further embodiment of the method, after successful verification of the user authorization, the anonymized patient dataset is transmitted in combination with the patient identification dataset. Thereby, for example, the technical advantage is achieved that the person identification data may be displayed in combination with the patient examination data.

In a further embodiment of the method, after non-successful verification of the user authorization merely the anonymized patient dataset is transmitted. Thereby, for example, the technical advantage is achieved that the anonymity of the patient data is maintained.

In a further embodiment of the method, the anonymized patient dataset and the patient identification dataset are transmitted from the external data storage to a wireless mobile terminal or a personal computer. Thereby, for example, the technical advantage is achieved that the patient examination data may be reviewed mobile or on a workplace.

In a further embodiment of the method, the external data storage is remotely provided in a network. Thereby, for example, the technical advantage is achieved that a network storage may be used for storing the patient data and this is not affected by a failure of the internal data storage.

In a further embodiment of the method, the external data storage sends a message to connected units in response to receiving the anonymized patient dataset and/or the patient identification dataset. Thereby, for example, the technical advantage is achieved that the connected devices may be informed about the presence of new patient datasets.

In a further embodiment of the method, a message for receiving the patient dataset is sent to the internal data storage. Thereby, for example, the technical advantage is achieved that the internal data storage may provide the patient data in response to the message.

In a further embodiment, the object is solved by an apparatus for transmitting medical datasets, including computer program code configured for receiving a patient dataset that includes patient identification data and patient examination data from an internal data storage. The computer program code is configured for generating an anonymized patient dataset by segregating the patient identification data from the received patient dataset and for generating an encrypted patient identification dataset on the basis of the segregated patient identification data. The computer program code is configured for transmitting the anonymized patient dataset and the encrypted patient identification dataset to an external data storage. Thereby, the same technical advantages are achieved as by the method according to the first aspect.

BRIEF DESCRIPTIONS OF THE DRAWINGS

Exemplary embodiments are depicted in the figures and are discussed in detail in the following.

DETAILED DESCRIPTION

Figure 1:
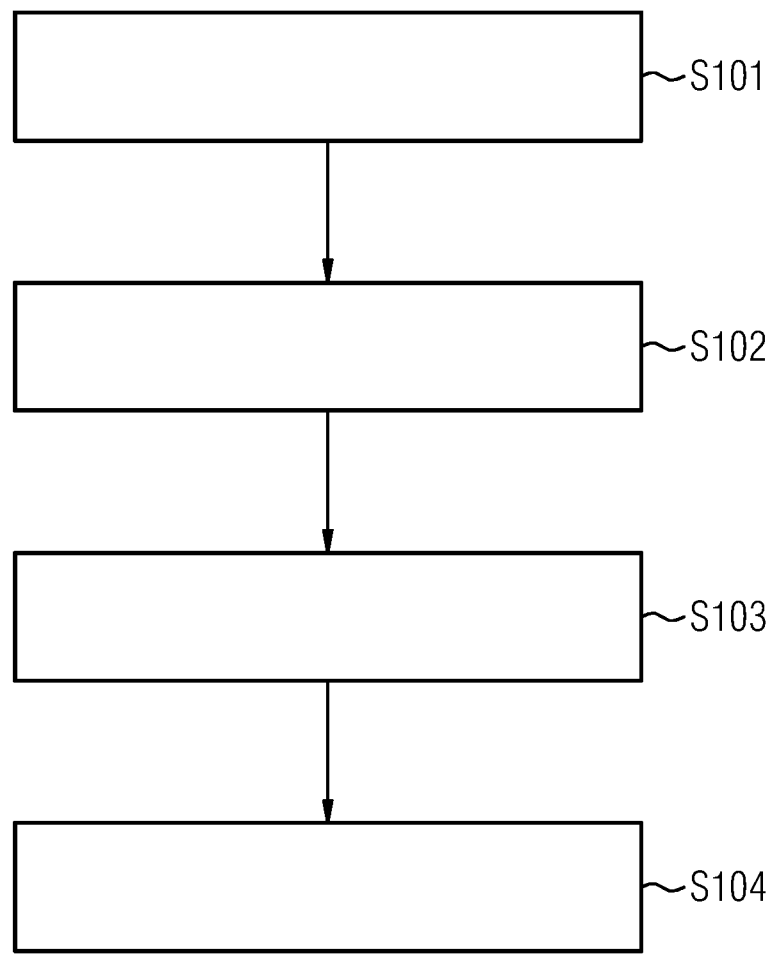
FIG. 1 depicts a block diagram of an example of a method for transmitting medical datasets.

FIG. 1 depicts a block diagram of a method for transmitting medical datasets. The method includes the acts of receiving S101 a patient dataset that includes patient identification data as well as patient examination data. The patient dataset is received from an internal data storage, for example, from a picture archiving and communications system PACS of a hospital. In act S102, an anonymized patient dataset is generated by segregating the patient identification data from the received patient dataset. In act S103, an encrypted patient identification dataset is generated on the basis of the segregated patient identification data. In act S104, the anonymized patient dataset, as well as the encrypted patient identification dataset, is transmitted to an external data storage, for example, to a network storage or a cloud in the internet.

Figure 2:
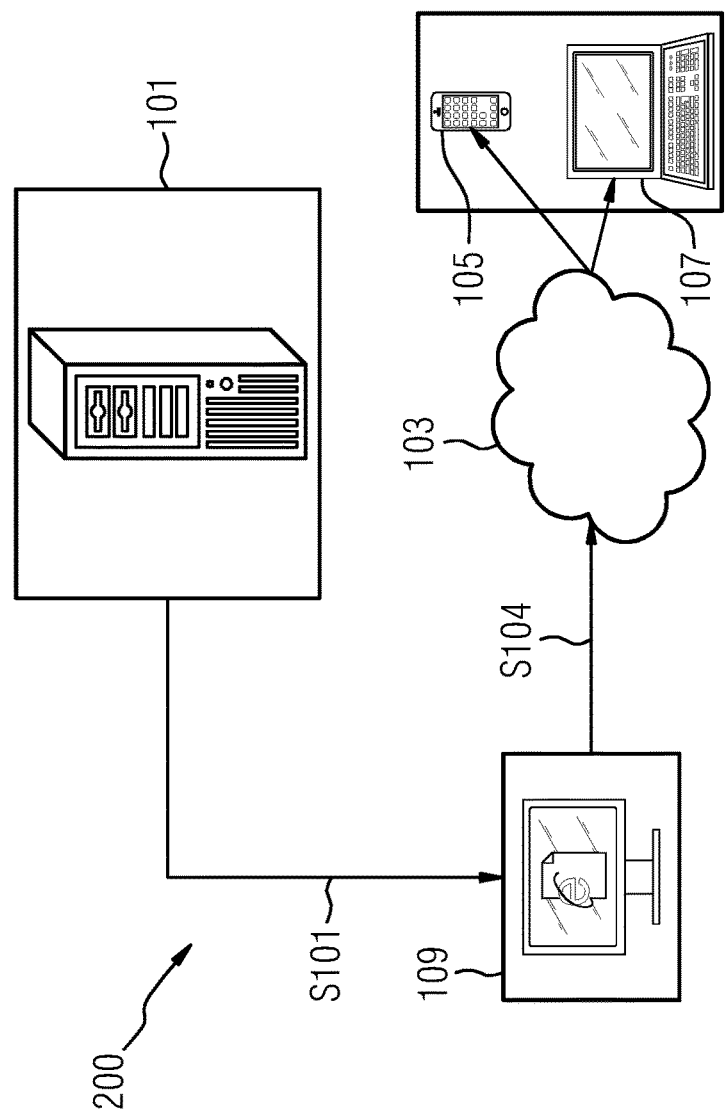
FIG. 2 depicts a schematic view of an example of a computer system.

FIG. 2 depicts a schematic view of a computer system 200 having an application 109. The hospital stores private patient identification data in conjunction with medical patient examination data in patient datasets that are obtained in the medical examinations. The obtained patient dataset is stored in an internal data storage 101 of the hospital.

The internal data storage 101 may be composed of a picture archiving and communication system PACS, a radiology information system RIS, a hospital information system HIS, a storage of imaging devices, workstations, relational databases, a fixed content storage system, or individual computer files.

Under certain conditions, the stored patient dataset may be accessible for medical personal outside the hospital. For example, expert physicians are consulted in order to assess lab results or medical images or make a diagnosis. In another case, the patient resides outside of his regular residence area and another hospital requests the medical patient data that are stored in the local hospital of the patient. Thus, the other hospital requires an access to the medical information databases within the local hospital in order to make a reliable diagnosis. In a further case, the patient may seek an advice of a physician outside the hospital to obtain a second opinion. The patients may also want to keep the patient data for future use and for archiving a course of disease. Thus, it is advisable to render accessible the patient data in an external data storage instead of for example on a CD.

The data storage 101 serves as internal data storage of the hospital, in which the original patient datasets are stored. For example, images that are gained from imaging medical devices are stored in the PACS Server as a data storage 101.

The original patient data sets are transmitted in act S101 to an application 109. The application 109 pulls the patient data sets having the patient identification data and the patient examination data by way of a message from the PACS-Server. Thus, the application 109 gathers the patient data sets from the PACS server and removes afterwards the patient identification data from the received patient datasets in order to generate new anonymized patient data sets. The anonymized patient data sets include merely patient examination data. The segregated patient identification data are additionally stored and encrypted by the application 109 as patient identification dataset, for example, in a JSON-file In act S104, the anonymized patient dataset is transmitted in combination with the separate, encrypted patient identification dataset to the cloud 103 as external data storage. The anonymized patient dataset and the patient identification dataset may be retrieved from the cloud 103 using a personal computer 107 or a mobile terminal 105.

Consequently, the patient identification data are separated from the DICOM-files. The patient identification data of a study, (like name, age, sex, or date of birth), are stored as separate JSON-file with encryption. The encrypted JSON-file and the anonymized DICOM-file having the pictures and reports are uploaded by the application 109 into the cloud. Thus, the application 109 serves as a communication hub between the hospital institutions, the picture archiving, and communication system PACS and visualizing systems.

When a user logs in into the system and has a user authorization for viewing the patient identification data, the encrypted patient identification data of the JSON-file are downloaded to the client and displayed. If a user does not have the required user authorization for viewing the patient identification data, the patient identification data are not displayed.

The user may share the patient dataset with other users, radiologists, or patients each with or without the patient identification data. Since the patient identification data are only downloaded, when the corresponding user authorization is given, the sharing of the study between radiologists or physicians is connected with high data security.

Figure 3:
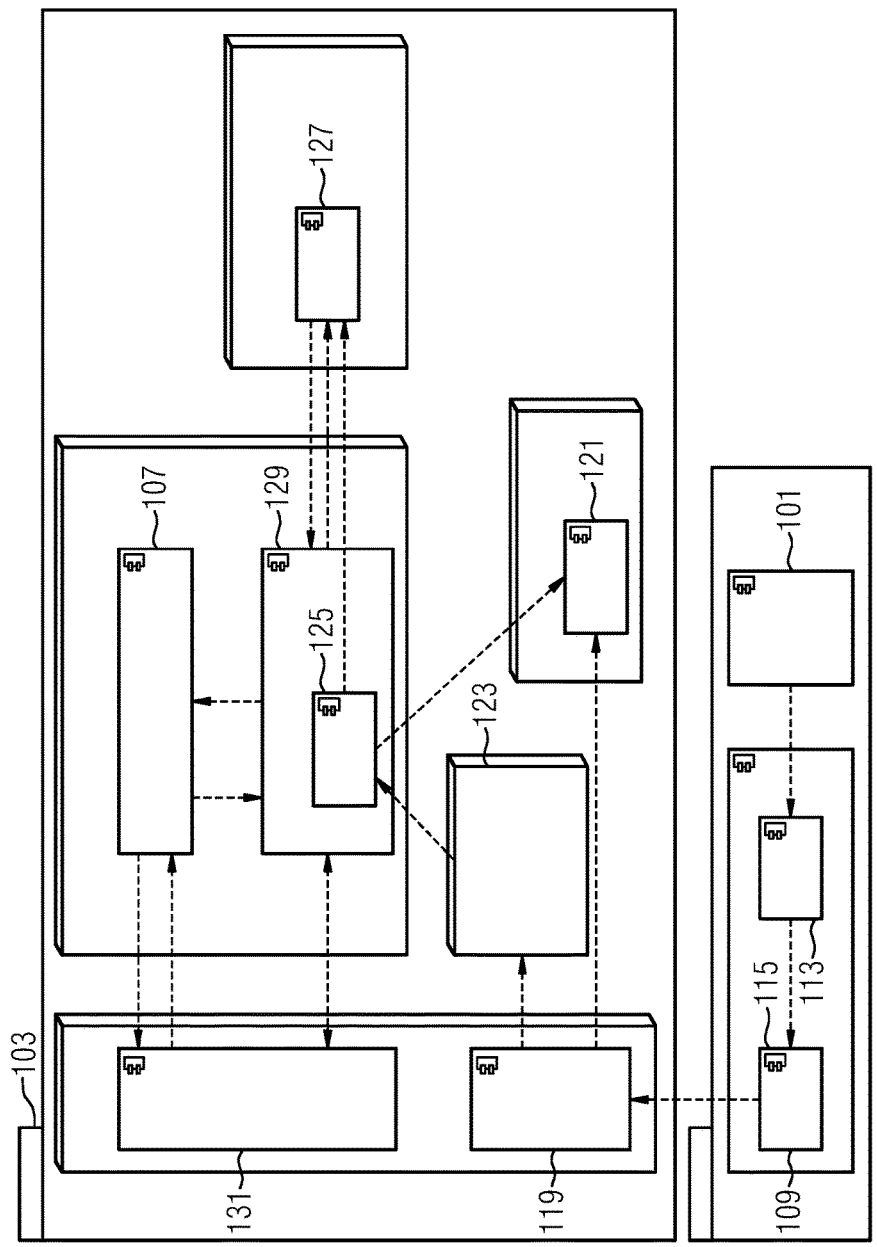
FIG. 3 depicts an example of a component diagram of the cloud-based system.

FIG. 3 depicts a component diagram the cloud-based systems for reproducing and sharing the patient data sets. In the hospital institution, the DICOM-files stored in the PACS-Server of the hospital are transmitted to the application 109. The application 109 has two components, namely a receiver 113 for receiving the DICOM-files from the PACS server 101 and an uploader 115 having an anonymizer. The anonymizer segregates the patient identification data from the DICOM-files, stores these in a separate JSON-file, and encrypts the JSON-file. The uploader 115 uploads the anonymized DICOM-file and the encrypted JSON-file into the cloud 103.

The cloud 103 includes an uploading service 119 that receives the DICOM-file and the encrypted JSON-file from the uploader 115 and stores these into the BLOB storage 121 of the Cloud 103. The uploading service 119 updates the service bus 123 about the new patient data. The service bus 123 notifies all registered units of the presence of the new patient data.

A picture web service 125 receives the notification of the new patient data, accesses the newly uploaded DICOM-files, and generates picture files in PNG format, which correspond to the pixel information of the DICOM-file and the JSON-file having the metadata. The picture file and the JSON-file having the Metadata serve for viewing the patient data in the client. The picture web service 125 generates a database 127 with information about the uploaded images.

A picture service 129 provides the end points, on which a client 107 may access to the patient data that the picture web service 125 has generated in correspondence to the DICOM-file and that have been uploaded into the cloud 103. An authorization server 131 provides that the data request originates from authorized users. The client 107 validates the user, receives the patient data from the picture web service 125, and displays the patient data. The client provides the possibility to share the patient data with other authorized users.

Figure 4:
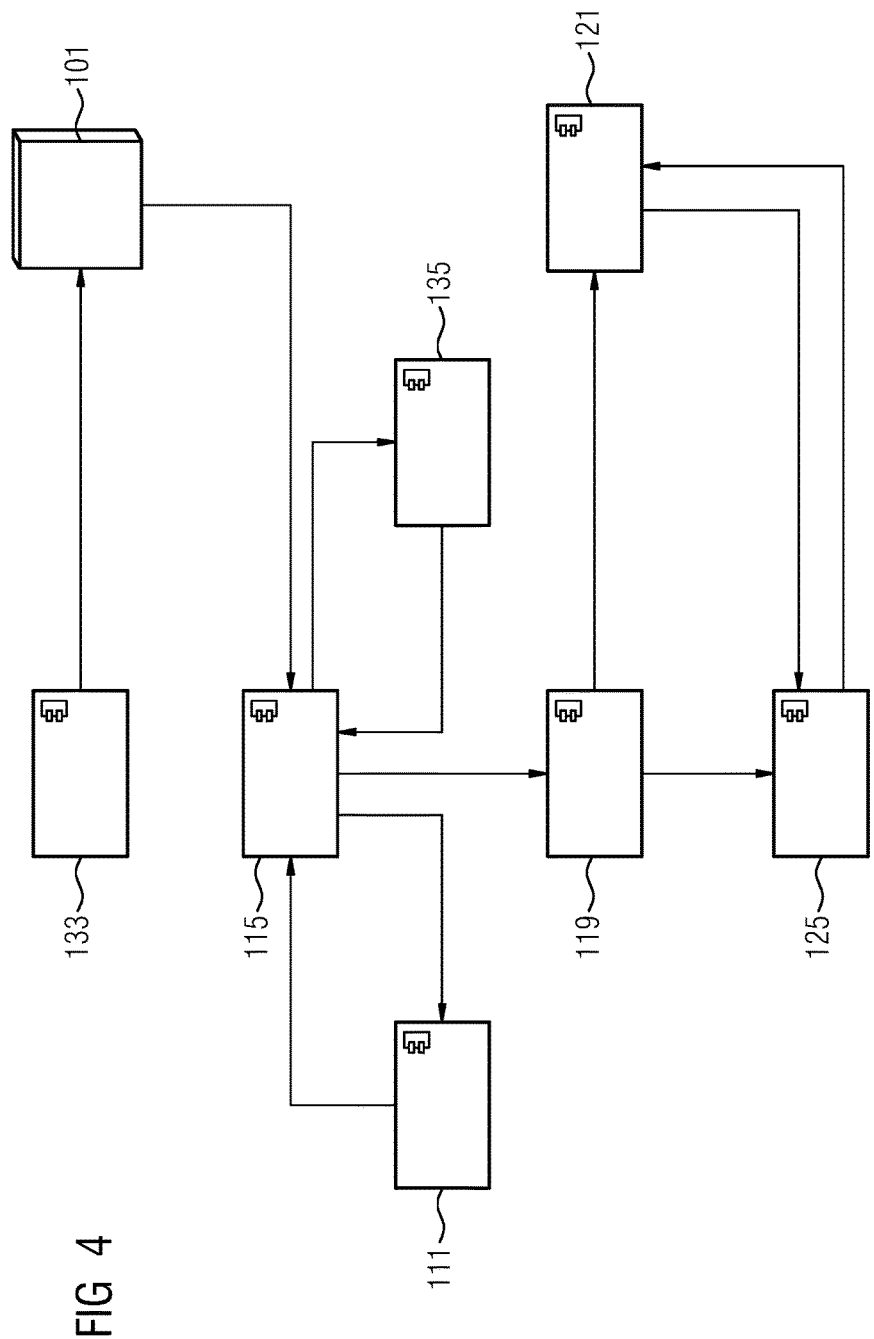
FIG. 4 depicts an example of a data flow diagram of the cloud-based system.

FIG. 4 depicts a data flow diagram of the cloud-based systems. The patient data sets are generated by an imaging medical device 133 and transmitted to the PACS-Server 101 of the hospital. The patient data sets are transferred to the uploader 115 and transmitted to the anonymizer 135. The anonymizer 135 segregates the patient identification data from the patient datasets and returns the patient identification data as separate patient identification dataset in form of a JSON-file. Beside this, the anonymizer 135 returns a DICOM-file as anonymized patient dataset to the uploader 115. The JSON-file is transmitted from the uploader 115 to an encrypter 111 that encrypts the JSON-file and returns this to the uploader 115.

The uploader 115 uploads the anonymized DICOM-file and the JSON-file to the uploading service 119 of the cloud 103. The uploading service 119 stores the anonymized DICOM-file and the JSON-file in the BLOB-storage 121 (BLOB—Binary Large Object). Additionally, the uploading service 119 sends a message to the picture web service 125. The picture web service 125 receives the message about the new patient data, accesses the newly uploaded DICOM-files of the BLOB-storage 121, and generates picture files in PNG-Format. The picture files are also transmitted to the BLOB-storage 121 afterwards.

Figure 5:
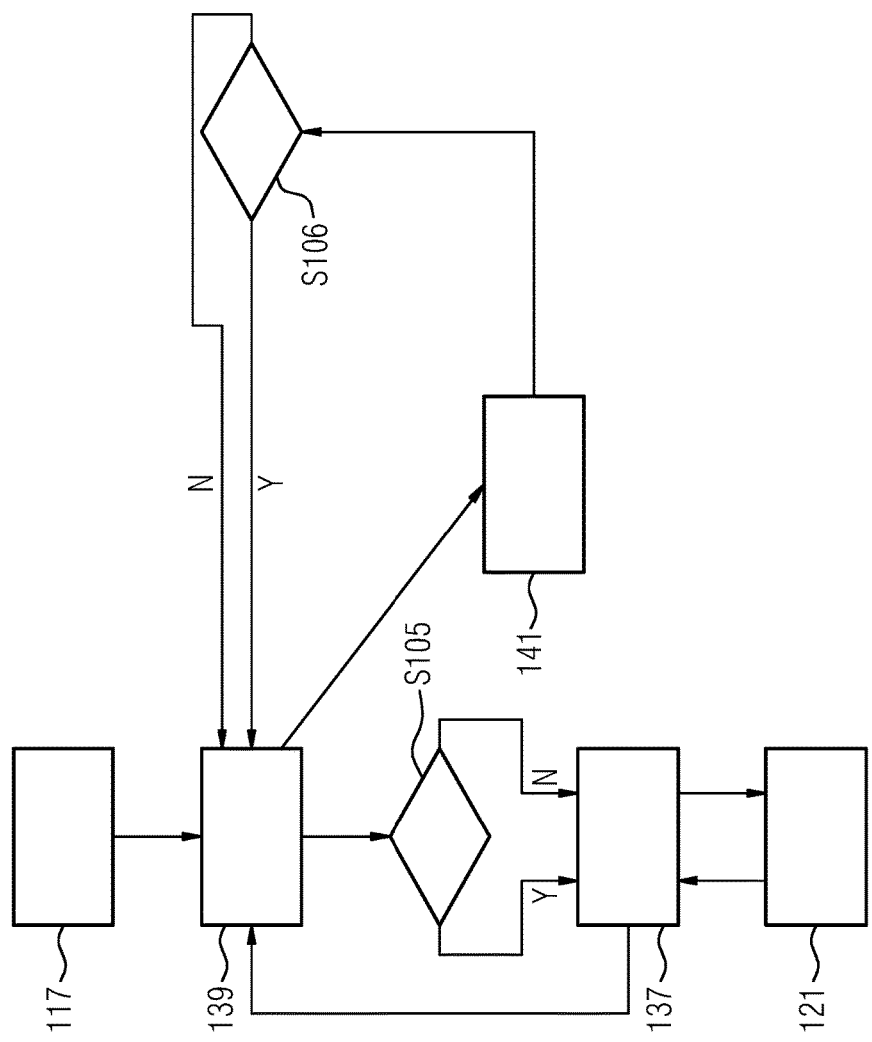
FIG. 5 depicts an example of a further data flow diagram of the cloud-based system.

FIG. 5 depicts a further data flow diagram of the cloud-based system for displaying, storing and sharing the patient data sets by segregating the patient identification data. When a user 117 logs in, the client decides on the basis of the user authorization in act S105, whether to download the encrypted patient identification dataset from the BLOB-storage 121 via an storage service 137 or not. If the user 117 has an admissible user authorization, the encrypted JSON-file and the anonymized DICOM-file are transmitted to an inbox 139. If the user has no admissible user authorization, only the anonymized DICOM-file is transferred to the inbox 139.

An information builder 141 retrieves the patient data from the inbox 139. In act S106 is tested, whether the patient identification dataset is present. If this is the case, the encrypted JSON-file as well as the anonymized DICOM-file is read. The client decrypts the JSON-file in order to display the patient identification data in combination with the corresponding patient examination data. If this is not the case, only the anonymized DICOM-file is read and displayed.

Figure 6:
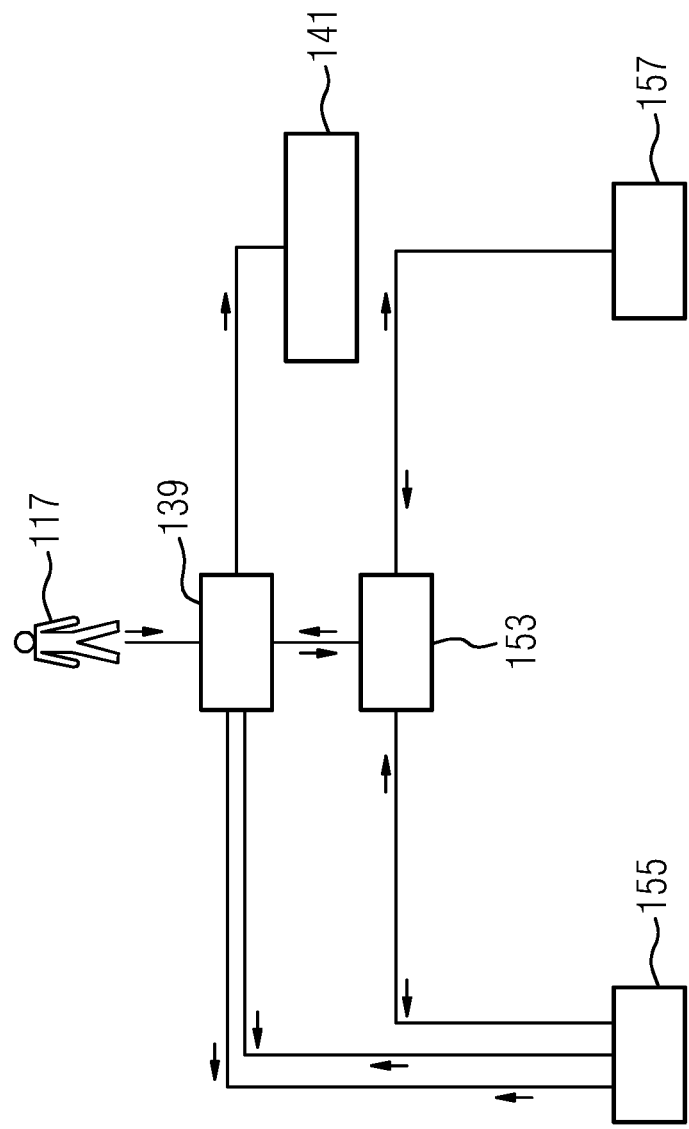
FIG. 6 depicts an example of a component diagram for transmitting studies.

FIG. 6 depicts a component diagram for transmitting studies. The patient identification data are segregated from the DICOM-files, encrypted, and uploaded into the cloud. When a user 117 logs in at the Client for viewing the patient data, a decision is made on the basis of the login data, to download the encrypted patient identification dataset or not.

The inbox 139 sends a request to the access service 153 for downloading the encrypted patient identification dataset, if the login data are admissible. The access service 153 uses the storage access service 155 for downloading the encrypted patient identification dataset. For the sake of performance, the encrypted patient identification dataset may be deposited in a cache-storage. The information in the patient identification dataset is decrypted only in the cache of the browsers and returned to the inbox 139. In addition to the storage access service 155, a web storage may be used for storing the files in a cache storage in order to increase performance. Beside this, the access service 153 is in contact with a decryption service 157 that decrypts the patient identification dataset.

Instead of storing the patient identification data and the patient examination data in the inbox 139, a structure having the required original information may be stored and cleaned accordingly.

After downloading the remaining patient data, the inbox 139 sends a request to the information builder service 141 to build the original information that is to be displayed in the user interface. The information builder service 141 hides the file content structure and the complexity of building the information to be shown from the rest of the systems. The information builder service 141 is used to decouple the controller from the JSON-Structure. Further modifications at the JSON-structure only require modification of this service.

If the user 117 does not have the required login data for reading the patient identification dataset available, the inbox 139 only loads the anonymized patient dataset having the patient examination data and sends a request to the information builder service 141, to build the information from the available patient examination data.

Figure 7:
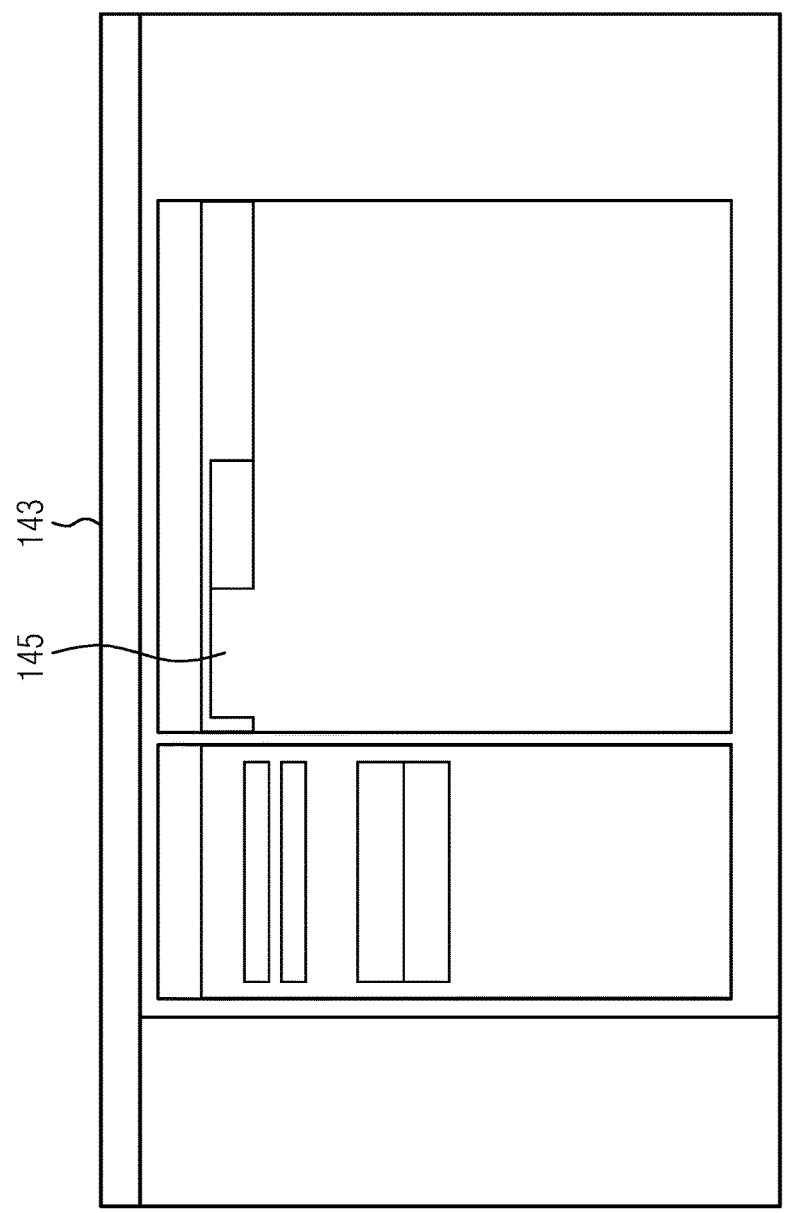
FIG. 7 depicts an example of a user interface for generating studies without patient identification data.

FIG. 7 depicts a graphical user interface 143 for reproducing studies without patient identification data. The studies are displayed in a window 145 as summary or in an original format.

Figure 8:
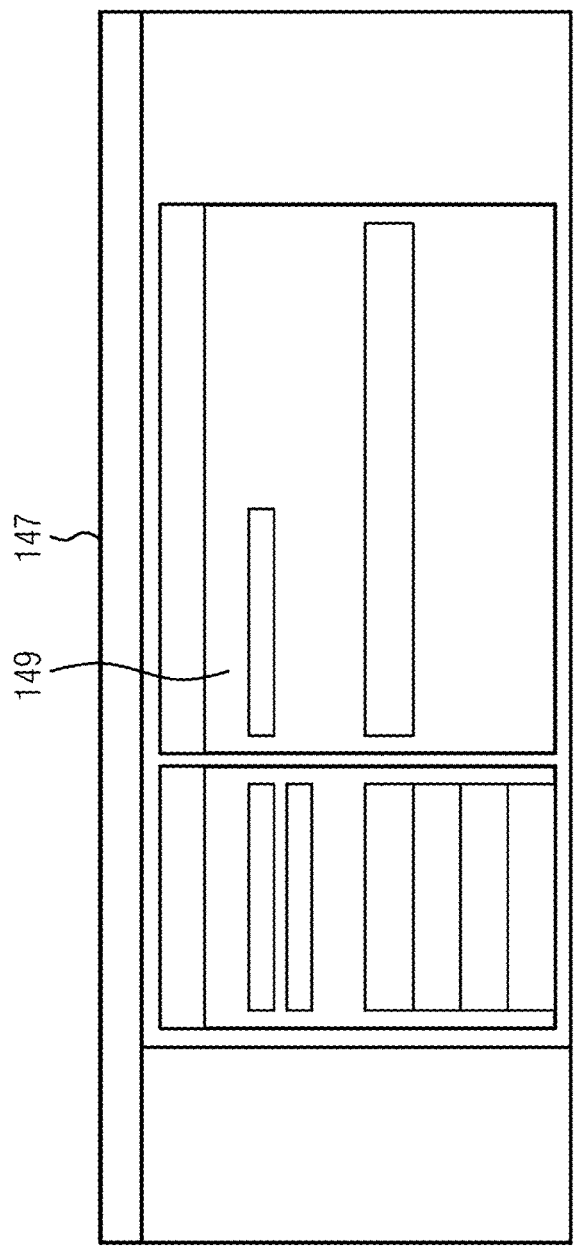
FIG. 8 depicts an example of a user interface for transmitting studies without patient identification data.

FIG. 8 depicts a user interface 147 for transmitting patient datasets without patient identification data. In a window 149, an email-address is provided, to which the anonymized patient data sets are to be transferred. In addition, a message to the recipient is input.

The cloud-based computer system serves for segregating the patient identification data from the patient examination data in the patient datasets. The anonymized patient data sets may be reproduced, stored, and encrypted. The anonymized patient datasets, for example, include picture data that are generated by different devices, for example, by a computer tomography device, a magnetic resonance device, an ultrasonic device, or nuclear medical devices.

The original patient data sets are stored in digital form using a DICOM storage and transmission protocol (DICOM—Digital Imaging and Communications in Medicine), in order to combine the original systems, server, and network computer with a picture archiving- and communications system. The original patient data sets include DICOM-Metadata in a binary computer readable form.

A specific subset of this DICOM-Metadata includes fields having patient identification data, which form a protected health Information. In the DICOM format, pictures may be stored in groups of pictures, which are denoted as series. A group of series again forms a study. Each picture may be represented by an individual binary file including picture data and binary header information. The binary header information includes metadata with and without protected health information.

When these pictures are reproduced, stored, or transmitted from a hospital having a PACS- or DICOM server to a different hospital or a remote digital storage system, like for example, to a different PACS- or DICOM-Server, patient confidentiality plays an important role.

A user employs the method or the computer system with a cloud-based data storage and a cloud-based reproduction software in order to store, view or share the patient data. The patient identification data are segregated from the patient data and encrypted in a separate file.

The method has the advantage that all patient data may be stored securely in the cloud and a user may retrieve these via connections in the entire world. Since the patient identification data are segregated and encrypted, confidentiality of the patient examination data is maintained. Nonetheless, hospitals may share anonymized information, such as pictures or clinical reports. The user may view and share the patient data on different devices, such as tablet PCs, laptops, or personal computers. The patient may keep his medication, his pictures, and his course of disease for personal purposes. This may be used for all imaging devices within a medical institution.

The above-described method may be implemented via a computer program product including one or more readable storage media having stored thereon instructions executable by one or more processors of the computing system. Execution of the instructions causes the computing system to perform operations corresponding with the acts of the method described above.

The instructions for implementing processes or methods described herein may be provided on computer-readable storage media or memories, such as a cache, buffer, RAM, FLASH, removable media, hard drive, or other computer readable storage media. A processor performs or executes the instructions to train and/or apply a trained model for controlling a system. Computer readable storage media include various types of volatile and non-volatile storage media. The functions, acts, or tasks illustrated in the figures or described herein may be executed in response to one or more sets of instructions stored in or on computer readable storage media. The functions, acts or tasks may be independent of the particular type of instruction set, storage media, processor or processing strategy and may be performed by software, hardware, integrated circuits, firmware, micro code and the like, operating alone or in combination. Likewise, processing strategies may include multiprocessing, multitasking, parallel processing and the like.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for transmitting medical datasets, the method comprising:
   receiving a patient dataset from an internal data storage, the patient dataset comprising patient identification data and patient examination data;
   generating a DICOM file including an anonymized patient dataset by segregating the patient identification data from the received patient dataset, the anonymized patient dataset including a first logical link to an encrypted patient identification dataset;
   generating a JavaScript-Object-Notation-file including the encrypted patient identification dataset using the segregated patient identification data, the encrypted patient identification dataset including a second logical link to the anonymized patient dataset;
   storing the encrypted patient identification dataset in a separate file than the anonymized patient dataset; and
   verifying a user authorization;
   wherein after a non-successful verification of the user authorization, only the DICOM file is transmitted to an external data storage;
   wherein after a successful verification of the user authorization, the DICOM file and the JavaScript-Object-Notation-file are transmitted to the external data storage.

2. The method of claim 1, wherein the anonymized patient dataset and the encrypted patient identification dataset are stored separately in the external data storage.

3. The method of claim 1, wherein the anonymized patient dataset and the encrypted patient identification dataset are stored in the internal data storage.

4. The method of claim 1, wherein the anonymized patient dataset and the encrypted patient identification dataset are transmitted from the external data storage to a wireless mobile terminal or a personal computer.

5. The method of claim 1, wherein the external data storage is provided remotely in a network.

6. The method of claim 1, wherein the external data storage sends a message to connected units in response to receiving the anonymized patient dataset, the encrypted patient identification dataset, or the anonymized patient dataset and the encrypted patient identification dataset.

7. The method of claim 1, wherein a message for receiving the patient dataset is sent to the internal data storage.

* * * * *